United States Patent [19]

Gaffar et al.

[11] 4,118,474

[45] Oct. 3, 1978

[54] ANTIBACTERIAL ORAL COMPOSITION

[75] Inventors: Abdul Gaffar, Somerset; Hollandra P. Niles, Newark, both of N.J.

[73] Assignee: Colgate-Palmolive Company, New York, N.Y.

[21] Appl. No.: 714,717

[22] Filed: Aug. 16, 1976

[51] Int. Cl.² .......................... A61K 7/22; A61K 7/16
[52] U.S. Cl. ........................................ 424/54; 424/57; 424/49
[58] Field of Search .................... 424/49–54, 424/81

[56] References Cited

U.S. PATENT DOCUMENTS

| 3,325,402 | 6/1967 | Mortimer | 424/81 |
| 3,431,208 | 3/1969 | Bailey | 424/49 |
| 3,703,583 | 11/1972 | Martin | 424/54 |
| 3,925,456 | 12/1975 | Ploger et al. | 424/54 |
| 3,941,772 | 3/1976 | Ploger et al. | 424/54 |
| 4,042,679 | 8/1977 | Gaffar | 424/54 |

OTHER PUBLICATIONS

Hargreaves et al., "Antimicrobial . . . Products", Chem. Abstracts, vol. 82, 1975, para. 153831q.

*Primary Examiner*—Henry R. Jiles
*Assistant Examiner*—Cary Owens
*Attorney, Agent, or Firm*—Herbert S. Sylvester; Murray M. Grill; Robert L. Stone

[57] ABSTRACT

An antibacterial oral composition effective to promote oral hygiene containing an antibacterial antiplaque agent and an additive which reduces staining of dental surfaces without substantially diminishing the antibacterial and antiplaque activity of the agent. Bis-biguanido hexanes, such as chlorhexidine and alexidine, and quaternary ammonium salts, such as benzethonium chloride and cetyl pyridinium chloride, are typical examples of antibacterial agents. The antistain additive is phosphonoacetic acid or salts thereof.

14 Claims, No Drawings

ANTIBACTERIAL ORAL COMPOSITION

This invention relates to an antibacterial oral composition which promotes oral hygiene.

Cationic antibacterial materials are well known in the art. See, for instance the section on "Quaternary Ammonium and Related Compounds" in the article on "Antiseptics and Disinfectants" in Kirk-Othmer Encyclopedia of Chemical Technology, 2nd edition (Vol. 2, p. 632–635), incorporated herein by reference. Cationic materials which possess antibacterial activity (i.e., are germicides) are used against bacteria and have been used in oral compositions to counter plaque formation caused by bacteria in the oral cavity.

Among the most common of these antibacterial antiplaque quaternary ammonium compounds is benzethonium chloride, also known as Hyamine 1622 or diisobutylphenoxyethoxyethyl dimethyl benzyl ammonium chloride. In an oral preparation this material is highly effective in promoting oral hygiene by reducing formation of dental plaque and calculus, which is generally accompanied by a reduction in caries formation and periodontal diseases. Other cationic antibacterial agents of this type are those mentioned, for instance, in U.S. Pat. Nos. 2,984,639, 3,325,402, 3,431,208 and 3,703,583, and British Pat. No. 1,319,396.

Other antibacterial antiplaque quaternary ammonium compounds include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, cetyl pyridinium chloride and quaternized 5-amino-1,3-bis (2-ethylhexyl)-5-methyl hexa hydro-pyrimidine are typical quaternary ammonium antibacterial agents.

Other types of cationic antibacterial agents which are desirably incorporated in oral compositions to promote oral hygiene by reducing plaque formation are the amidines such as the substituted guanidines, e.g., chlorhexidine and the corresponding compound, alexidine, having 2-ethylhexyl groups instead of chlorophenyl groups and other bis-biguanides such as those described in German patent application No. P 2,332,383 published Jan. 10, 1974, which sets forth the following formula:

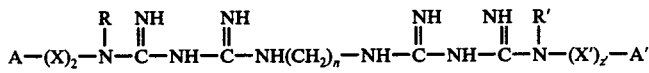

in which A and A' signify as the case may be either (1) a phenyl radical, which as substituent can contain up to 2 alkyl or alkoxy groups with 1 up to about 4 C-atoms, a nitro group or a halogen atom, (2) an alkyl group which contains 1 to about 12 C-atoms, or (3) alicyclic groups with 4 to about 12 C-atoms, X and X' as the case may be may represent an alkylene radical with 1–3 C-atoms, z and z' are as the case may be either 0 or 1, R and R' as the case may be may represent either hydrogen, an alkyl radical with 1 to about 12 C-atoms or an aralkyl radical with 7 to about 12 C-atoms, n is a whole number of 2 to inclusively 12 and the polymethylene chain $(CH_2)_n$ can be interrupted by up to 5 ether, thioether, phenyl- or naphthyl groups; these are available as pharmaceutically suitable salts. Additional substituted guanidines are: N'-(4-chlorobenzyl)-$N^5$-(2,4-dichlorobenzyl) biguanide; p-chlorobenzyl biguanide, 4-chlorobenzhydryl guanylurea; N-3-lauroxypropyl-$N^5$-p-chlorobenzyl biguanide; 5,6-dichloro-2-guanidobenzimidazole; and N-p-chlorophenyl-$N^5$-laurylbiguanide.

The long chain tertiary amines also possess antibacterial and antiplaque activity. Such antibacterial agents include tertiary amines having one fatty alkyl group (typically 12 to 18 carbon atoms) and 2 poly(oxyethylene) groups attached to the nitrogen (typically containing a total of from 2 to 50 ethenoxy groups per molecule) and salts thereof with acids and compounds of the structure:

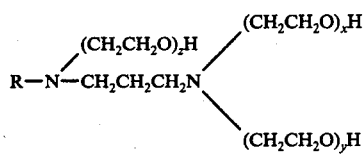

where R is a fatty alkyl group containing 12 to 18 carbon atoms and x, y and z total 3 or higher, as well as salts thereof. Generally, cationic agents are preferred for their antiplaque effectiveness.

The antibacterial antiplaque compound is preferably one which has an antibacterial activity such that its phenol coefficient is well over 50, more preferably well above 100, such as above about 200 or more for S. aureus; for instance the phenol coefficient (A.O.A.C.) of benzethonium chloride is given by the manufacturer as 410, for S. aureus. The cationic antibacterial agent will generally be a monomeric (or possibly dimeric) material molecular weight well below 2,000, such as less than about 1,000. It is, however, within the broader scope of the invention to employ a polymeric cationic antibacterial agent. The cationic antibacterial is preferably supplied in the form of an orally acceptable salt thereof, such as the chloride, bromide, sulfate, alkyl sulfonate such as methyl sulfonate and ethyl sulfonate, phenylsulfonate, such as p-methylphenyl sulfonate, nitrate, acetate, gluconate, etc.

The cationic antibacterial agents and long chain tertiary amine antibacterial agents effectively promote oral hygiene, particularly by removing plaque. However, their use has been observed to lead to staining of dental surfaces or discoloration.

The reason for the formation of such dental stain has not been clearly established. However, human dental enamel contains a high proportion (about 95%) of hydroxyapatite which includes $Ca^{+2}$ and $PO_4^{-3}$ ions. In the absence of dental plaque additional $Ca^{+2}$ and $PO_4^{-3}$, particularly from saliva, can be deposited on the enamel and such deposits can include color bodies which ultimately stain the tooth enamel as a calcified deposit thereon. It can be that as the cationic or long chain tertiary amine antibacterial agents remove plaque they also denature protein from saliva in the oral environment and the denatured protein can then act as a nucleating agent which is deposited on and stains or discolors tooth enamel.

Previously employed additives which reduced dental staining by cationic antibacterial antiplaque agents also generally reduced the activity of the antibacterial agents or its ability to act on dental plaque to measurable degrees. Further Victamide (also known as Victamine C) which is the condensation product of ammonia with phosphorus pentoxide actually increases staining even in the absence of a cationic antibacterial antiplaque agent and it and other known phosphorus containing agents such as disodium-ethane-1-hydroxy-1,1-diphosphonic acid salt precipitate in the presence of antibacterial agent such as bis-biguanido compound, thereby reducing the antiplaque effectiveness of the antibacterial agent.

It is an advantage of this invention that an anti-nucleating additive is provided which prevents staining of dental enamel without substantially adversely affecting antibacterial and antiplaque activity of a cationic or long chain tertial amine antibacterial agent. Other advantages will be apparent from consideration of the following disclosure.

In accordance with certain of its aspects this invention relates to an oral composition comprising an oral vehicle, a cationic or long chain tertiary amine antibacterial antiplaque agent and phosphonoacetic acid (PAA), of the formula $H_2O_3P-CH_2-COOH$, or an orally acceptable salt such as with an alkali metal (e.g., sodium and potassium), ammonium, $C_1-C_{18}$ mono-di-and tri-substituted ammonium (e.g., alkanol substituted such as mono-di-and tri-ethanolammonium) cation.

Antibacterial agents which are cationic or long chain amine germicides which may be employed in the practice of this invention are described above. They are typically employed in amounts such that the oral product contains between about 0.001% and 15% by weight of the agent. Preferably for desired levels of antiplaque effect, the finished oral product contains about 0.01 to about 5%, and most preferably about 0.025% to 1.0% by weight of the agent. These amounts refer to the quantity of the free base form of the agent.

The stain which generally occurs on dental enamel is unexpectedly prevented when phosphonoacetic acid or water-soluble salt thereof, is employed. This material is an anti-nucleating agent. In itself (even in the absence of cationic antiplaque anti-bacterial agents) it is effective to reduce formation of dental calculus without unduly decalcifying enamel. However, not all anti-nucleating agents are effective to prevent stain by cationic antibacterial agents. Victamide actually increases staining even in the absence of an antibacterial antiplaque agent.

U.S. Pat. No. 3,934,002 discloses combination of the above-described bis-biguanide antiplaque agents with various anti-calculus agents, some of which contain phosphono and/or carboxy groups, but none corresponding to the phosphonoacetic acid additive compound employed herein.

The concentration of phosphonoacetic acid (or salt) in the oral compositions can range widely, typically upward from 0.01% by weight. There is no upper limit on the amount that can be utilized except as dictated by cost or incompatibility with the vehicle. Generally, concentrations from about 0.01 to about 10% by weight are utilized. Oral compositions which in the ordinary course of usage could be accidentally ingested preferably contain lower concentrations of phosphonoacetic acid. Thus, a mouthwash in accordance with this invention preferably contains less than 3% by weight of phosphonoacetic acid. Dentifrice compositions, topical solutions and prophylactic pastes, the latter to be administered professionally, can contain from 0.01 to 10% by weight, preferably from 0.1 to 5% by weight of phosphonoacetic acid. Most desirably, the phosphonoacetic acid is present in a molar excess relative to the amount of antibacterial antiplaque agent(based on the free base thereof, in order to best prevent staining by the antibacterial antiplaque agent.

In certain highly preferred forms of the invention the oral composition may be substantially liquid in character, such as a mouthwash or rinse. In such a preparation the vehicle is typically a water-alcohol mixture. Generally, the ratio of water to alcohol is in the range of from about 1:1 to about 20:1 preferably from 3:1 to 20:1 and most preferably about 17:3, by weight. The total amount of water-alcohol mixture in this type of preparation is typically in the range of from about 70 to about 99.9% by weight of the preparation. The pH of such liquid preparations is generally in the range of from about 4.5 to about 9 and typically from about 5.5 to 8. The pH is preferably in the range of from about 6 to about 8.0. It is noteworthy that the composition of the invention permits the use of the phosphonoacetic acid at a pH below 5 without substantially decalcifying dental enamel.

Such liquid oral preparations may also contain a surface active agent and/or a fluorine-providing compound.

In certain other desirable forms of this invention, the oral composition may be substantially solid or pasty in character, such as a toothpowder, a dental tablet or a toothpaste or dental cream. The vehicle of such solid or pasty oral preparations contains polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicates, silica, bentonite, and mixtures thereof. Preferred polishing materials include crystalline silica having particle sizes of up to 5 microns, a mean particle size of up to 1.1 microns, and a surface area of up to 50,000 $cm^2/gm$. silica gel, complex amorphorus alkali metal aluminosilicate and hydrated alumina.

Alumina, particularly the hydrated alumina sold by Alcoa as C333, which has an alumina content of 64.9% by weight, a silica content of 0.008%, a ferric oxide content of 0.003%, and a moisture content of 0.37% at 110° C., and which has a specific gravity of 2.42 and a particle size such that 100% of the particles are less than 50 microns and 84% of the particles are less than 20 microns, is particularly desirable.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so called "water-insoluble" polishing materials are anionic in character and also include small amounts of soluble material. Thus, insoluble sodium metaphosphate may be formed in any suitable manner, as illustrated by Thorpe's *Dictionary of Applied Chemis-*

*try*, Volume 9, 4th Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble sodium metaphosphate, may be reduced by washing with water if desired. The insoluble alkali metal metaphosphate is typically employed in powder form of a particle size such that no more than 1% of the material is larger than 37 microns.

The polishing material is generally present in amounts ranging from about 20 to about 99% by weight of the oral preparation. Preferably, it is present in amounts ranging from about 20 to about 75% in toothpaste, and from about 70 to about 99% in toothpowder.

In the preparation of toothpowders, it is usually sufficient to admix mechanically, e.g., by milling, the various solid ingredients in appropriate quantities and particle sizes.

In pasty oral preparations the above-described combination of the antibacterial antiplaque agent and phosphonoacetic acid compound should be compatible with the other components of the preparation. Thus, in a toothpaste, the liquid vehicle may comprise water and humectant typically in an amount ranging from about 10 to about 90% by weight of the preparation. Glycerine, sorbitol, or polyethylene glycol may also be present as humectants or binders. Particularly advantageous liquid ingredients comprise mixtures of water, glycerine and sorbitol.

In clear gels where the refractive index is an important consideration, about 3–30% by weight of water, 0 to about 80% by weight of glycerine, and about 20–80% by weight of sorbitol is preferably employed. A gelling agent, such as natural or synthetic gums or gumlike materials, typically Irish moss, sodium carboxymethylcellulose, methyl cellulose, or hydroxyethyl cellulose, may be employed. Other gelling agents which may be employed include gum tragacanth, polyvinylpyrrolidone and starch. They are usually present in toothpaste in amount up to 10% by weight, preferably in the range of from about 0.05 to about 5%. The preferred gelling agents are methyl cellulose and hydroxyethyl cellulose. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to about 9, generally about 5.5 to about 8 and preferably about 6 to about 8.0, may also contain a surface active agent and/or a fluorine-providing compound.

It will be understood that, as is conventional, the oral preparations are to be sold or otherwise distributed in suitably labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

In oral compositions such as mouthrinses and toothpastes, a surfactant is often present, e.g., to promote foaming. It will be understood that it is preferable to employ nonionic surfactants rather than their anionic counterparts. Examples of water-soluble nonionic surfactants are condensation products of ethyleneoxide with various compounds reactive therewith having long hydrophobic chains (e.g., aliphatic chains of 12 to 20 carbon atoms) which condensation products ("ethoxamers") have hydrophilic polyoxyethylene moieties, such as condensation products of ethylene oxide and fatty acids, fatty alcohols, fatty amides, including alcohols such as sorbitan monostearate or polypropyleneoxide (that is Pluronic materials).

In certain forms of this invention, a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be a nontoxic amount. In a solid oral preparation, such as a toothpaste or tooth powder, an amount of such compound which releases a maximum of 1% by weight of the preparation is considered satisfactory. Any suitable minimum amount of such compound may be used, but it is preferable to employ sufficient compound to release from 0.005 to 1%, and preferably about 0.1% of fluoride ion. Typically, in the cases of alkali metal fluorides and stannous fluoride, this component is present in an amount up to 2% by weight, based on the weight of the preparation, and preferably in the range of from 0.05 to 1%. In the case of sodium monofluorophosphate, the compound may be present in an amount up to 7.6% by weight, more typically 0.76%.

In a liquid oral preparation such as a mouthwash, the fluorine-providing compound is typically present in an amount sufficient to release up to 0.13%, preferably from 0.0013 to 0.1% and most preferably from 0.0013 to 0.05%, by weight, of fluoride ion.

Various other materials may be incorporated in the oral preparations of this invention. Examples are whitening agents, preservatives, silicones, chlorophyll compounds, and ammoniated material such as urea, diammonium phosphate, and mixtures thereof. These adjuvants, where present, are incorporated in the preparation in amounts which do not substantially adversely affect the properties and characteristics desired.

Any suitable flavoring or sweetening material may also be employed. Examples of suitable flavoring constituents are flavoring oils, e.g., oils of spearmint, peppermint, wintergreen, sassafras, clove, sage, eucalyptus, marjoram, cinnamon, lemon and orange, and methyl salicylate. Suitable sweetening agents include sucrose, lactose, maltose, sorbitol, sodium cyclamate, perillartine, and saccharin. Suitably, flavor and sweetening agents may together comprise from 0.01 to 5% or more of the preparation.

In preparing the oral compositions of this invention in an oral vehicle which typically includes water, it is highly desirable, if not essential, to add the PAA compound after the other ingredients (except perhaps some of the water) are mixed or contacted with each other to avoid a tendency towards formation of a precipitate.

For instance, a mouthrinse or mouthwash may be prepared by mixing ethanol and water with flavoring oil, nonionic surfactant humectant, cationic antibacterial antiplaque agent, such as benzethonium chloride or chlorhexidine, sweetener and color and then adding the phosphonoacetic acid or a water-soluble salt (e.g., sodium salt) thereof and additional water as desired.

A toothpaste may be prepared by forming a gel with humectant, gum or thickener such as hydroxyethyl cellulose, sweetener and adding thereto polishing agent, flavor, antibacterial agent, such as benzethonium chloride or chlorhexidine, and additional water, followed by addition of the phosphonoacetic acid or water-soluble salt thereof. If sodium carboxymethyl cellulose is employed as the gelling agent the procedure of either U.S. Pat. No. 3,842,168 or U.S. Pat. No. 3,843,779, modified by the inclusion of the phosphonoacetic acid is followed.

In the practice of this invention an oral composition according to the invention, such as a mouthwash or toothpaste containing cationic or long chain amine antibacterial antiplaque agent in amount effective to promote oral hygiene, and phosphonoacetic acid compound in amount effective to reduce staining of dental surfaces otherwise resulting from the presence of the antibacterial antiplaque agent is applied regularly to dental enamel, preferably from about 5 times per week to about 3 times daily, at a pH of about 4.5 to about 9, generally about 5.5 to about 8, preferably about 6 to 8.

The following specific examples are further illustrative of the nature of the present invention, but it is understood that the invention is not limited thereto. The compositions are prepared in the usual manner and all amounts and proportions referred to herein and in the appended claims are by weight unless otherwise indicated.

EXAMPLES 1–7

The following mouthwash formulation is prepared and tested:

| Mouthwash Formulation | Parts |
|---|---|
| Flavored alcohol | 15 |
| Pluronic F 108 (polyalkene oxide block polymer) | 3 |
| Glycerine | 10 |
| Benzethonium chloride (BC) | 0.075 |
| Sodium saccharin | 0.03 |
| Phosphonoacetic acid (PAA) | x |
| Water | Q.S. to 100 |
| pH 7.0 (adjusted with 5N NaOH) | |
| Appearance, stability | Clear |

The PAA, and about 10 parts of the water, are added to the other previously mixed ingredients. Tooth staining characteristics are tested by slurrying hydroxyapatite (Biogel) with salivary protein and acetaldehyde and a pH 7 phosphate buffer. The mixture is shaken at 37° C. until a light brown color is formed, which colored material is separated. Color levels are determined on a Gardner Color Difference Meter before and after the test composition is applied to the colored material.

The following TABLE I shows the antistain results when the indicated amounts ($x$) of PAA are employed in the above mouthwash formulation.

TABLE I

| | ANTISTAIN | | |
|---|---|---|---|
| Example | Parts (x) PAA | Reflectance | Reflectance Difference |
| 1 | 0 | 39.0 | 0 |
| 2 | 0.1 | 56.0 | 17.0 |
| 3 | 0.2 | 54.0 | 15.0 |
| 4 | 0.3 | 56.0 | 17.0 |
| 5 | 0.4 | 53.0 | 14.0 |
| 6 | 0.5 | 55.0 | 16.0 |
| 7 | 1.0 | 53.0 | 14.0 |

The above results plainly establish that PAA, at all levels of $x$, substantially and significantly reduces dental staining ordinarily produced by BC. These tests are conducted with the pH adjusted to about 7.0, the pH prior to adjustment ranging from about 3.5 to 4.6. Formulations adjusted to pH ranging from about 5 to 8 yield similar results.

EXAMPLES 8–14

Substitution of equivalent amounts of the following antibacterial antiplaque agents for the BC employed in Examples 2–7 yield formulations also producing unexpected reductions in dental staining.

| Example | Antibacterial Antiplaque Agent |
|---|---|
| 8 | Chlorhexidine diacetate |
| 9 | Chlorhexidine digluconate |
| 10 | Alexidine dihydrochloride |
| 11 | Dodecyl trimethyl ammonium bromide |
| 12 | Benzyl dimethyl stearyl ammonium chloride |
| 13 | Cetyl pyridinium chloride |
| 14 | $C_{12-18}$ alkyl-N(CH$_2$CH$_2$OH)—CH$_2$CH$_2$N(CH$_2$CH$_2$OH)—CH$_2$CH$_2$OH |

It is further notable that the antiplaque activity of the above-exemplified formulations containing PAA are substantially equal to corresponding formulations without the PAA.

The following formulations exemplify toothpastes with antiplaque activity and reduced staining:

| | Example | |
|---|---|---|
| | 15 | 16 |
| Hydrated Alumina | 30 (parts) | 30 |
| Glycerine | 16 | 16 |
| Sorbitol (70%) | 6 | 6 |
| Pluronic F-108 | 3 | 3 |
| Hydroxyethyl cellulose | 1.2 | 1.2 |
| Benzethonium chloride | 0.5 | — |
| Chlorohexidine digluconate (20%) | — | 4.725 |
| Phosphonoacetic acid | 2 | 2 |
| Sodium saccharin | 0.17 | 0.17 |
| Flavor | 0.8 | 0.8 |
| Water | Q.S. to 100 | Q.S. to 100 |

This invention has been disclosed with respect to preferred embodiments and it will be understood that variations and modifications thereof obvious to those skilled in the art are to be included within the spirit and purview of this application and the scope of the appended claims.

What is claimed is:

1. An oral composition comprising an oral vehicle, at least one nitrogen containing antibacterial antiplaque agent selected from the group consisting of cationic bis-guanido and quaternary ammonium antibacterial antiplaque agents and phosphonoacetic acid or an orally acceptable salt thereof.

2. The oral composition of claim 1 wherein said antibacterial antiplaque agent is present in amount to provide about 0.001 to about 15% by weight based on the free base form of said agent and said phosphono compound is present in amount of about 0.01 to about 10% by weight.

3. The oral composition of claim 2 wherein said antibacterial antiplaque agent is present in amount of about 0.01 to about 5% by weight based on the free base form of said agent and said phosphono compound is present in a molar excess relative to said agent.

4. The oral composition of claim 2 wherein said antibacterial antiplaque agent is a bis-quanido antiplaque agent.

5. The oral composition of claim 4 wherein said antibacterial antiplaque agent is a pharmaceutically acceptable water soluble salt of an agent selected from the group consisting of chlorhexidine and alexidine.

6. The oral composition of claim 5 wherein said antibacterial antiplaque agent is a pharmaceutically acceptable water soluble salt of chlorhexidine.

7. The oral composition of claim 2 wherein said antibacterial antiplaque agent is benzethonium chloride.

8. The oral composition of claim 2 wherein said antibacterial antiplaque agent is a quaternary ammonium compound containing 1 to 2 alkyl groups of 8 to 20 carbon atoms.

9. The oral composition of claim 8 wherein said antibacterial antiplaque agent is cetyl pyridinium chloride.

10. The oral composition of claim 1 wherein said vehicle comprises a liquid vehicle and a gelling agent and a dentally acceptable polishing material is present and said composition is a toothpaste of pH of about 4.5 to about 9.

11. The oral composition of claim 1 wherein said vehicle is an aqueous-alcohol and said composition is a mouthwash of pH of about 4.5 to about 9.

12. The mouthwash composition of claim 11 comprising about 0.01 to about 5.0% based on its free base weight of benzethonium chloride and relative thereto, a molar excess within the range of about 0.1 to about 5% by weight of phosphonoacetic acid or an orally acceptable salt thereof.

13. The mouthwash composition of claim 11 comprising about 0.01 to about 5% based on its free base weight of a water-soluble pharmaceutically acceptable salt of chlorhexidine, and relative thereto, a molar excess within the range of about 0.1 to about 5% by weight of phosphonoacetic acid or an orally acceptable salt thereof.

14. A method of preparing an oral composition as defined in claim 1 wherein said phosphono compound is added to the remaining components of said composition after said components have been contacted with each other.

* * * * *